US008361443B2

(12) United States Patent
Cuthbertson

(10) Patent No.: US 8,361,443 B2
(45) Date of Patent: *Jan. 29, 2013

(54) PEPTIDE-BASED COMPOUNDS

(75) Inventor: Alan Cuthbertson, Oslo (NO)

(73) Assignee: GE Healthcare AS, Oslo (NO)

( * ) Notice: Subject to any disclaimer, the term of this patent is extended or adjusted under 35 U.S.C. 154(b) by 1108 days.

This patent is subject to a terminal disclaimer.

(21) Appl. No.: 11/570,090

(22) PCT Filed: Jun. 15, 2005

(86) PCT No.: PCT/NO2005/000209
§ 371 (c)(1),
(2), (4) Date: Dec. 6, 2006

(87) PCT Pub. No.: WO2005/123767
PCT Pub. Date: Dec. 29, 2005

(65) Prior Publication Data
US 2009/0263320 A1 Oct. 22, 2009

(30) Foreign Application Priority Data

Jun. 16, 2004 (NO) .................................. 20042523
Jun. 25, 2004 (NO) .................................. 20042704

(51) Int. Cl.
*A61K 49/04* (2006.01)

(52) U.S. Cl. ...... 424/9.4; 424/1.11; 424/1.65; 424/1.81; 424/1.85; 424/1.89; 424/9.1; 424/1.69

(58) Field of Classification Search ................. 424/1.11, 424/1.65, 1.69, 1.81, 1.85, 1.89, 9.1, 9.3, 424/9.4, 9.5, 9.6, 9.7, 9.8; 530/300, 316, 530/317, 328, 331; 534/7, 10–16; 514/1, 514/9, 11

See application file for complete search history.

(56) References Cited

U.S. PATENT DOCUMENTS

| 6,906,171 | B2 * | 6/2005 | Cuthbertson | ................. 530/336 |
| 7,351,790 | B2 * | 4/2008 | Cuthbertson et al. | ......... 530/317 |
| 7,368,474 | B2 * | 5/2008 | Cuthbertson et al. | ......... 514/453 |
| 7,410,943 | B2 * | 8/2008 | Cuthbertson et al. | ............. 514/2 |
| 7,521,419 | B2 * | 4/2009 | Cuthbertson et al. | ........... 514/10 |
| 7,608,243 | B2 * | 10/2009 | Cuthbertson et al. | ........ 424/1.69 |

FOREIGN PATENT DOCUMENTS

| WO | 01/77145 | 10/2001 |
| WO | 03/006491 | 1/2003 |
| WO | 2005/003166 | 1/2005 |

OTHER PUBLICATIONS

PCT/NO2005/000209 International Search Report and Written Opinion dated Oct. 6, 2005.

* cited by examiner

*Primary Examiner* — D L Jones
(74) *Attorney, Agent, or Firm* — Yonggang Ji

(57) ABSTRACT

The invention relates to new peptide-based compounds for use as diagnostic imaging agents or as therapeutic agents wherein the agents comprise targeting vectors which bind to integrin receptors.

11 Claims, No Drawings

US 8,361,443 B2

PEPTIDE-BASED COMPOUNDS

This application is a filing under 35 U.S.C. 371 of international application number PCT/NO2005/000209, filed Jun. 15, 2005, which claims priority to application number 20042523 filed Jun. 16, 2004 and 20042704 filed Jun. 25, 2004, in Norway the entire disclosure of which is hereby incorporated by reference.

FIELD OF INVENTION

The present invention relates to new peptide-based compounds and their use in therapeutically effective treatments as well as for diagnostic imaging techniques. More specifically the invention relates to the use of such peptide-based compounds as targeting vectors that bind to receptors associated with angiogenesis, in particular integrin receptors, e.g. the $\alpha v\beta 3$ integrin receptor. Such contrast agents may thus be used for diagnosis of for example malignant diseases, heart diseases, endometriosis, inflammation-related diseases, rheumatoid arthritis and Kaposi's sarcoma. Moreover such agents may be used in therapeutic treatment of these diseases.

BACKGROUND OF INVENTION

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimetre size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for anti tumour therapy.

The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Further examples of undesired conditions that are associated with neovascularization or angiogenesis, the development or proliferation of new blood vessels are shown below. Reference is also made in this regard to WO 98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous malformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

Angiogenesis involves receptors that are unique to endothelial cells and surrounding tissues. These markers include growth factor receptors such as VEGF and the Integrin family of receptors. Immunohistochemical studies have demonstrated that a variety of integrins perhaps most importantly the $\alpha_v$ class are expressed on the apical surface of blood vessels [Conforti, G., et al. (1992) Blood 80: 37-446] and are available for targeting by circulating ligands [Pasqualini, R., et al. (1997) Nature Biotechnology 15: 542-546]. The $\alpha 5\beta 1$ is also an important integrin in promoting the assembly of fibronectin matrix and initiating cell attachment to fibronectin. It also plays a crucial role in cell migration [Bauer, J. S., (1992) J. Cell Biol. 116: 477-487] as well as tumour invasion and metastasis [Gehlsen, K. R., (1988) J. Cell Biol. 106: 925-930].

The integrin $\alpha v\beta 3$ is one of the receptors that is known to be associated with angiogenesis. Stimulated endothelial cells appear to rely on this receptor for survival during a critical period of the angiogenic process, as antagonists of the $\alpha v\beta 3$ integrin receptor/ligand interaction induce apoptosis and inhibit blood vessel growth.

Integrins are heterodimeric molecules in which the $\alpha$- and $\beta$-subunits penetrate the cell-membrane lipid bilayer. The $\alpha$-subunit has four $Ca^{2+}$ binding domains on its extracellular chain, and the $\beta$-subunit has a number of extra cellular cysteine-rich domains.

Many ligands (eg. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. (Ruoslahti, J. Clin. Invest., 87: 1-5 (1991)). Perhaps the most widely studied effect of RGD peptides and mimetics thereof relate to their use as anti-thrombotic agents where they target the platelet integrin GpIIbIIIa.

Inhibition of angiogenesis in tissues by administration of either an $\alpha v\beta 3$ or $\alpha v\beta 5$ antagonist has been described in for example WO 97/06791 and WO 95/25543 using either antibodies or RGD containing peptides. EP 578083 describes a series of mono-cyclic RGD containing peptides and WO 90/14103 claims RGD-antibodies. Haubner et al. in the J. Nucl. Med. (1999); 40: 1061-1071 describe a new class of tracers for tumour targeting based on monocyclic RGD containing peptides. Biodistribution studies using whole-body autoradiographic imaging revealed however that the $^{125}$I-labelled peptides had very fast blood clearance rates and predominantly hepatobiliary excretion routes resulting in high background.

Cyclic RGD peptides containing multiple bridges have also been described in WO 98/54347 and WO 95/14714. Peptides derived from in vivo biopanning (WO 97/10507) have been used for a variety of targeting applications. The sequence CDCRGDCFC (RGD-4C), has been used to target drugs such as doxorubicin (WO 98/10795), nucleic acids and adenoviruses to cells (see WO 99/40214, WO 99/39734, WO 98/54347, WO 98/54346, U.S. Pat. No. 5,846,782). Peptides containing multiple cysteine residues do however suffer from the disadvantage that multiple disulphide isomers can occur. A peptide with 4 cysteine residues such as RGD-4C has the possibility of forming 3 different disulphide folded forms. The isomers will have varying affinity for the integrin receptor as the RGD pharmacophore is forced into 3 different conformations.

Further examples of RGD comprising peptide-based compounds are found in WO 01/77145, WO 02/26776 and WO 03/006491, the content of which are incorporated herein by reference.

The efficient targeting and imaging of integrin receptors associated with angiogenesis in vivo demands therefore a selective, high affinity RGD type vector that is chemically robust and stable. Furthermore, the route of excretion is an important factor when designing imaging agents in order to reduce problems with background. These stringent conditions are met by the bicyclic structures described in the present invention.

SUMMARY OF THE INVENTION

The present invention provides new peptide based compounds useful in treatment and diagnostic imaging of diseases associated with angiogenesis. Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous alformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

Further the present invention provides peptide based compounds useful in the diagnosis of cancer and other diseases involving angiogenesis such as those mentioned above, comprising a targeting moiety incorporating an imageable moiety. The imageable moiety can be any imageable moiety which when administered to a subject can generate an image of at least a part of said subject to which said peptide based compound has distributed, e.g. by radio imaging, SPECT, positron emission tomography (PET), magnetic resonance imaging (MRI), X-ray, optical imaging (OI), ultrasound (US), electrical impedance or magnetometric imaging modalities.

The present invention further provides methods of treatment of diseases associated with angiogenesis and methods of imaging of said diseases and also methods of monitoring of progression of treatment for such diseases. The invention further provides novel pharmaceutical compositions and precursors for the preparation of diagnostic contrast agents. Kits of contrast agents, in particular kits for the preparation of radiopharmaceutical contrast agents are also provided.

The peptide based compounds of the invention comprise a peptide vector, an optional linker $W_1$ and one moiety $Z_1$ or $Z_2$ as described by formula (I):

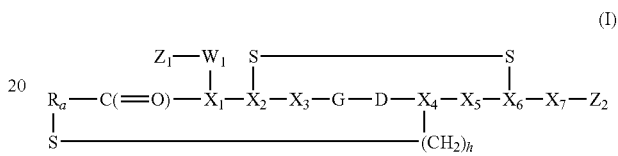

(I)

and pharmaceutically acceptable salt thereof
wherein
G represents glycine
D represents aspartic acid
$R_a$ represents —$(CH_2)_n$— or —$(CH_2)_n$—$C_6H_4$— wherein
n represents a positive integer 1 to 10
h represents a positive integer 1 or 2
$X_1$ represents an amino acid residue wherein said amino acid possesses a functional side-chain such as an acid or amine,
$X_2$ and $X_6$ represent independently amino acid residues together forming a disulphide bond,
$X_3$ represents arginine, N-methylarginine or an arginine mimetic,
$X_4$ represents a thiol-containing amino acid residue, and
$X_5$ represents a hydrophobic amino acid or derivatives thereof, and
$X_7$ represents a biomodifier moiety or is absent
at least one of $Z_1$ or $Z_2$ is present and represents an antineoplastic agent, or an imageable moiety and
$W_1$ represents a spacer moiety or is absent.

DESCRIPTION OF THE INVENTION

Viewed from one aspect the invention provides new peptide-based compounds of formula (I) as defined in the claims. The peptide vector of the compound constitutes the targeting moiety which has affinity for integrin receptors, e.g. affinity for the integrin $\alpha v \beta 3$.

The compounds of formula (I) comprise two bridges, wherein one bridge forms a disulphide bond and the second bridge comprises a thioether (sulphide) bond and wherein the bridges fold the peptide moiety into an 'interlocking' configuration.

The compounds of the current invention thus have a maximum of one disulphide bridge per molecule moiety. Compounds defined by the present invention are surprisingly stable in vivo and under the conditions employed during labelling, e.g. during labelling with technetium.

These new compounds may be used in therapeutically effective treatments as well as for imaging purposes.

The new peptide-based compounds described in the present invention are defined by formula (I):

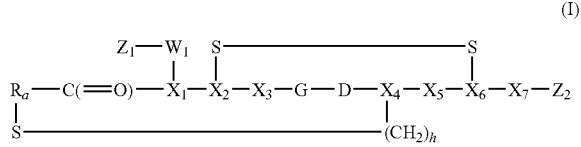

(I)

and physiologically acceptable salts thereof
wherein
G represents glycine, and
D represents aspartic acid, and
$R_a$ represents $—(CH_2)_n—$ or $—(CH_2)_n—C_6H_4—$, preferably $R_a$ represents $—(CH_2)—$,
and
n represents a positive integer between 1 and 10, and
h represents a positive integer 1 or 2, and
$X_1$ represents an amino acid residue wherein said amino acid possesses a functional side-chain such as an acid or amine preferentially aspartic or glutamic acid, lysine, homolysine, diaminopropionic acid or another diaminoalcylic acid,
$X_2$ and $X_6$ represent independently amino acid residues together forming a disulphide bond, the amino acid residues preferably independently represent a cysteine or a homocysteine residue, and
$X_3$ represents arginine, N-methylarginine or an arginine mimetic, preferably an arginine, and
$X_4$ represents a thiol-containing amino acid residue, preferably a cysteine or a homocysteine residue, and
$X_5$ represents a hydrophobic amino acid or derivatives thereof, preferably a tyrosine, a phenylalanine, a 3-iodo-tyrosine or a naphthylalanine residue, and more preferably a phenylalanine or a 3-iodo-tyrosine residue, and
$X_7$ is absent or represents a homogeneous biomodifier moiety preferably based on a monodisperse PEG building block comprising 1 to 10 units of said building block, said biomodifier having the function of modifying the pharmacokinetics and blood clearance rates of the said agents. In addition $X_7$ may also represent 1 to 10 amino acid residues preferably glycine, lysine, aspartic acid or serine. In a preferred embodiment of this invention $X_7$ represents a biomodifier unit comprised of polymerisation of the monodisperse PEG-like structure, 17-amino-5-oxo-6-aza-3,9,12,15-tetraoxaheptadecanoic acid of formula (II),

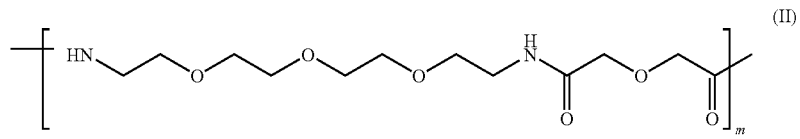

(II)

wherein m equals an integer from 1 to 10 and where the C-terminal unit is an amide or an acid moiety.

It is found that the biomodifier, $X_7$, modifies the pharmacokinetics and blood clearance rates of the compounds. The biomodifier effects less uptake of the compounds in tissue i.e. muscle, liver etc. thus giving a better diagnostic image due to less background interference. The secretion is mainly through the kidneys due to a further advantage of the biomodifier.

$W_1$ is absent or represents a spacer moiety and is preferentially derived from glutaric and/or succinic acid and/or a polyethyleneglycol based unit and/or a unit of formula (II) as illustrated above.

Other representative spacer ($W_1$) elements include structural-type polysaccharides, storage-type polysaccharides, polyamino acids and methyl and ethyl esters thereof, and polypeptides, oligosaccharides and oligonucleotides, which may or may not contain enzyme cleavage sites.

The role of the spacer moiety $W_1$ is to distance the relatively bulky imageable moiety from the active site of the peptide component. The spacer moiety $W_1$ is also applicable to distance a bulky antineoplastic agent from the active site of the peptide.

At least one of $Z_1$ and $Z_2$ is present and represents an antineoplastic agent or an imageable moiety. Z is herein after used to denote either one of or both $Z_1$ and $Z_2$.

For contrast agents useful in diagnosis and particularly in in vivo diagnosis the moieties Z comprise the imageable moiety or moieties. When the imageable moiety itself cannot be bound directly to $W_1$, $X_7$ or the peptide e.g. when the imageable moiety is a metal particle or a metal ion hereinafter denoted M, then Z comprises a moiety $A_1M$ wherein $A_1$ is a moiety capable of binding to $W_1$, $X_7$ or the peptide and at the same time carrying M. By carrying is meant any form of association between the moiety $A_1$ and M such as a chemical bond, e.g. covalent bond or electrovalent or ionic bonds or by absorption or any other type of association.

Chelating agents of formula (III) and (VII) hereinafter are also particularly preferred.

When M is a metal entity then $A_1$ represents a chelating agent, where the metal entity represents metal ion, paramagnetic metals, metal radio-nucleides, heavy metals and heavy metal oxides. The nature of Z and/or $A_1M$ will depend of the imaging modality utilised in the diagnosis. Z and/or $A_1M$ must be capable of detection either directly or indirectly in an in vivo diagnostic imaging procedure. eg. moieties which emit or may be caused to emit detectable radiation (eg. by radioactive decay, fluorescence excitation, spin resonance excitation, etc.), moieties which affect local electromagnetic fields (eg. paramagnetic, superparamagnetic, ferromagnetic or ferromagnetic species), moieties which absorb or scatter radiation energy (eg. chromophores, particles (including gas or liquid containing vesicles), heavy elements and compounds thereof, etc.), and moieties which generate a detectable substance (eg. gas microbubble generators).

A wide range of moieties suitable for detection in in vivo imaging are known from e.g. WO 98/47541, the content of which is incorporated by reference.

Imaging modalities and imageable moieties Z and M are described in more detail hereinafter:

In a first embodiment, Z of the compound of formula (I) comprises a moiety $A_1$ carrying one or more imageable moieties M useful in the Radio and SPECT imaging modality. Preferably M is a gamma emitter with low or no alpha- and beta-emission and with a half-life of more than one hour. Preferred groups M are the radionuclides $^{67}Ga$, $^{111}In$, $^{123}I$, $^{125}I$, $^{131}I$, $^{81m}Kr$, $^{99}Mo$, $^{99m}Tc$ $^{201}Tl$ and $^{133}Xe$. Most preferred is $^{99m}Tc$.

M can further be represented by the following isotopes or isotope pairs for use both in imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$; $^{47}Sc_{21}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

When M denotes a metallic radionuclide then $A_1$ denotes a chelating agent suitable for forming a stable chelate with M. Such chelating agents are well known from the state of art and typical examples of such chelating agents are described in Table I of WO 01/77145.

Particularly preferred are chelating agents of formula (III):

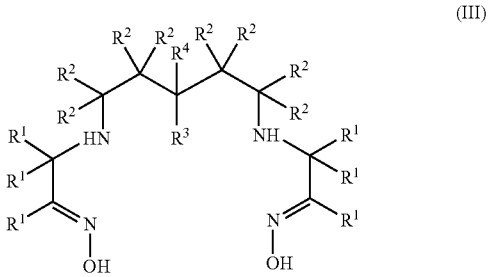

(III)

wherein:
each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents of formula (III) where $R^1$, $R^2$ and $R^3$ are hydrogen or methyl groups and $R^4$ is an alkylamine group, most specifically a compound of formula (IV).

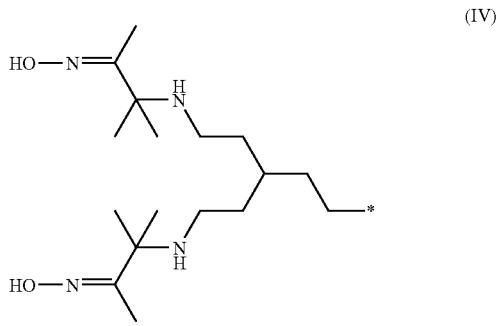 [SMILES: *CCC(CCNC(C)(C)C(C)=NO)CCNC(C)(C)C(C)=NO]

(IV)

Most preferably $A_1$ is the chelate of formula (IV) and the imaging moiety M is $^{99m}$Tc.

Other preferred chelating agents are of formula (V)

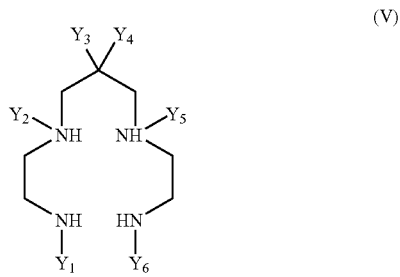

(V)

wherein $Y_1$-$Y_6$ independently represent H, alkyl, aryl or a combination thereof, where $Y_1$-$Y_6$ groups contain one or more functional moieties such that the chelate can be conjugated to $W_1$ or $X_7$ of the peptide-based compound of formula (I) e.g. preferably alkylamine, alkylsulphide, alkoxy alkyl carboxylate, arylamine, aryl sulphide or α-haloacetyl.

Non-metal radionuclides such as $^{123}$I, $^{125}$I and $^{131}$I may be covalently linked to $W_1$ when present or alternatively to $X_1$ by a substitution or addition reaction well known from the state of art.

In a second embodiment, the compound of formula (I) comprises a moiety Z useful in the PET imaging modality. Z then denotes a radioemitter with positron-emitting properties. Preferred groups Z are the radionuclides $^{11}$C, $^{18}$F, $^{13}$N, and $^{15}$O. $^{18}$F is specifically preferred. The metallic radioemitters $^{82}$Rb and $^{68}$Ga chelated with a chelating agent $A_1$ are also preferred.

Thiol coupling chemistry, $^{18}$F-synthons and labelled peptides prepared using the thiol coupling chemistry are described in WO 03/080544, the content of which is incorporated herein by reference.

Non-metal radionuclides such as $^{18}$F may be covalently linked to the moiety $W_1$ when present or alternatively to $X_1$ by a substitution or addition reaction well known from the state of art and also described eg. in WO03/080544 which is hereby incorporated by reference.

Description of peptides labelled by use of thiol coupling chemistry can be found in WO 2005/012335, the content of which is incorporated herein by reference.

In a preferred embodiment $A_1$ is the DOTA chelating agent and M is $^{68}$Ga which can be readily introduced in to the chelate using microwave chemistry.

In a third embodiment, the compound of formula (I) comprises a moiety $A_1$ carrying one or more imageable moieties M useful in the MR imaging modality. M here denotes a paramagnetic metal such as those mentioned in U.S. Pat. No. 4,647,447. $Gd^{3+}$, $Dy^{3+}$, $Fe^{3+}$ and $Mn^{2+}$ are particularly preferred and Z denotes a chelating agent, in particular a chelating agent such as acyclic or cyclic polyaminocarboxylates (e.g. DTPA, DTPA-BMA, DOTA and DO3A) as described e.g. in U.S. Pat. No. 4,647,447 and WO 86/02841. M may also denote metal oxides such as superparamagnetic, ferrimagnetic or ferromagnetic species which are absorbed by Z, e.g. such that Z function as a coating to the metal oxide. Metal oxides for use as MR contrast agents are described e.g. in U.S. Pat. No. 6,230,777 which is hereby incorporated by reference.

In a fourth embodiment the compound of formula (I) comprises a moiety $A_1$ carrying one or more imageable moieties M useful in the X-ray imaging modality. M here denotes a heavy metal such as W, Au and Bi preferably in the form of oxides. Z can also be represented by iodinated aryl derivatives particularly well known as X-ray contrast agents, e.g. Iopamiron™ and Omnipaque™. These agents can be linked via their amide or amine functions to the peptide of formula (I).

In a further embodiment the compound of formula (I) comprises Z in the form of gas filled microvesicles. Such ultrasound imaging agents can be utilised in the imaging of receptors e.g. when they are functionalised for binding to a peptide as described in the state of art e.g. in WO098/18500.

In a sixth embodiment of the present invention the moiety Z of formula (I) may be any moiety capable of detection either directly or indirectly in an optical imaging procedure. The detectable moiety can be a light scatterer (e.g. a coloured or uncoloured particle), a light absorber or a light emitter. More preferably Z is represented by a dye such as a chromophore or a fluorescent compound. The moiety Z can be any dye that interacts with light in the electromagnetic spectrum with wavelengths from the ultraviolet light to the near-infrared. In a preferred version Z has fluorescent properties.

Preferred organic dye moieties include groups having an extensive delocalized electron system, eg. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Further descriptions of moieties suitable in optical imaging procedures are found in WO 2005/003166 the content of which is hereby incorporated by reference.

In one aspect of the invention Z of formula (I) represents an antineoplastic agent. In this aspect the compound will target an angiogenic site associated with cancer and bring the antineoplastic agent to the diseased area.

The antineoplastic agent may be represented by cyclophosphamide, chloroambucil, busulphan, methotrexate, cytarabine, fluorouracil, vinblastine, paclitaxel, doxorubicin, daunorubicin, etoposide, teniposide, cisplatin, amsacrine, docetaxel, but a wide range of other antineoplastic agents may also be used.

The peptide vector of the peptide-based compound described herein has preferably no free amino- or carboxy-termini. This introduces into these compounds a significant increase in resistance against enzymatic degradation and as a result they have an increased in vivo stability as compared to many known free peptides.

As used herein the term 'amino acid' refers in its broadest sense to proteogenic L-amino acids, D-amino acids, chemically modified amino acids, N-methyl, Cα-methyl and amino acid side-chain mimetics and unnatural amino acids such as naphthylalanine. Any naturally occurring amino acid or mimetics of such natural occurring amino acids are preferred.

Some preferred embodiments of the compounds of formula (I) are illustrated by compounds below:

a compound of general formula (I) or a salt thereof, together with one or more pharmaceutically acceptable adjuvants, excipients or diluents.

The invention further provides a pharmaceutical composition for treatment of a disease comprising an effective amount of a compound of general formula (I), or an acid addition salt thereof, together with one or more pharmaceutically acceptable adjuvants, excipients or diluents.

A preferred embodiment of the invention relates to a radio-labelled agent of general formula (I), for use in diagnostic imaging.

The compounds according to the invention may be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

The compounds of formula (I) may be therapeutically effective in the treatment of disease states as well as detectable in in vivo imaging. Thus for example the peptide vector target the compound to the receptor and the imageable moiety Z may have therapeutic efficacy, e.g. by virtue of the radiotherapeutic effect of a radionuclide M bound to the compound through a chelating agent $A_1$.

Use of the compounds of formula (I) in the manufacture of therapeutic compositions (medicament) and in methods of therapeutic or prophylactic treatment, preferably treatment of cancer, of the human or animal body are thus considered to represent further aspects of the invention.

In one aspect of the invention the peptide-based compounds of formula (I) are used as contrast agents in diagnostic imaging.

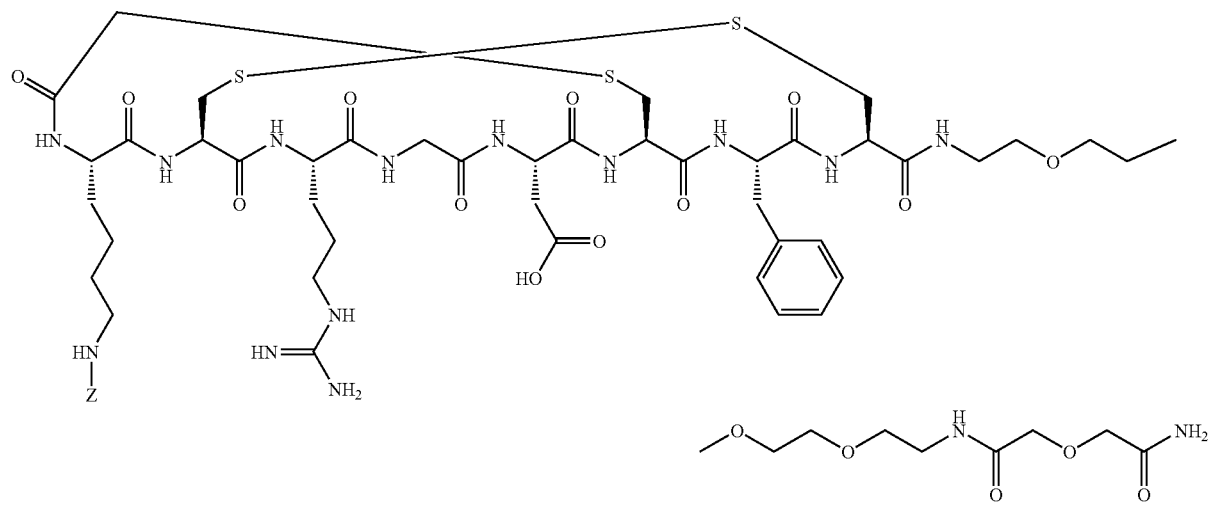

wherein Z is as defined above.

According to the present invention, any of the amino acid residues as defined in formula (I) may preferably represent a naturally occurring amino acid and independently in any of the D or L conformations.

In most cases, it is preferred that the amino acids in the peptide are all in the L-form. However, in some embodiments of the invention one, two, three or more of the amino acids in the peptide are preferably in the D-form. The inclusion of such D-form amino acids can have a significant effect on the serum stability of the compound.

The present invention also provides a pharmaceutical composition comprising an effective amount (e.g. an amount effective for enhancing image contrast in in vivo imaging) of Viewed from a further aspect the invention provides the use of a compound of formula (I) for the manufacture of a contrast agent for use in a method of diagnosis involving administration of said contrast agent to a human or animal body and generation of an image of at least part of said body.

Viewed from a still further aspect the invention provides a method of generating an image of a human or animal body involving administering a contrast agent to said body, e.g. into the vascular system and generating an image of at least a part of said body to which said contrast agent has distributed using scintigraphy, PET or SPECT modalities, MRI, X-ray, ultrasound or optical imaging wherein as said contrast agent is used a compound of formula (I).

Viewed from a still further aspect the invention provides a method of generating enhanced images of a human or animal body previously administered with a contrast agent composition comprising a compound as defined by formula I, which method comprises generating an image of at least part of said body.

Viewed from a further aspect the invention provides a method of monitoring the effect of treatment of a human or animal body with a drug to combat a condition associated with cancer, preferably angiogenesis, e.g. a cytotoxic agent, said method involving administering to said body a compound of formula (I) and detecting the uptake of said agent by cell receptors, preferably endothelial cell receptors and in particular $\alpha v\beta 3$ receptors, said administration and detection optionally but preferably being effected repeatedly, e.g. before, during and after treatment with said drug.

The compounds of the present invention can be synthesised using all the known methods of chemical synthesis but particularly useful is the solid-phase methodology of Merrifield employing an automated peptide synthesiser (J. Am. Chem. Soc., 85: 2149 (1964)). Typically, the desired sequences are assembled by solid-phase peptide synthesis. Standard procedures for the synthesis strategy employed for the examples of this invention are described in E. Atherton & R. C. Sheppard, "Solid phase peptide synthesis: a practical approach", 1989, IRL Press, Oxford.

For example, a resin with an acid-labile linker group, to which the desired amino-protected C-terminal amino acid residue has been esterified, is used. The amino protecting group is then removed and the second amino acid in the sequence is coupled using a suitable condensation reagent. Amino acids with semi-permanent amino protecting groups and permanent protecting groups for the functional side chains are employed. Amino-deprotection and coupling cycles are then repeated in alternating steps until the sequence of interest is assembled.

Alternatively, the peptides can be synthesised through solution peptide synthesis methods known in the art, either in a step-wise manner from the carboxyl terminus and/or through the application of segment condensation or ligation methods, employing comprehensive or minimal protection strategies. Combined solution-solid phase segment condensation approaches can also be applied.

Generally, the reactive side-chain groups present (for example amino, hydroxyl, guanidino and carboxyl groups) will be protected during overall synthesis as indicated above. A wide choice of protecting groups for amino acids is known (see, e.g., Greene, T. W. & Wuts, P. G. M. (1991) Protective groups in organic synthesis, John Wiley & Sons, New York). Amino protecting groups which may be employed include 9-fluorenylmethoxycarbonyl (Fmoc) and t-butyloxycarbonyl (Boc). Side-chain protecting groups which may be employed include t-butyl (tBu), trityl (Trt), Boc, and 2,2,5,7,8-pentamethylchroman-6-sulfonyl (Pmc). It will be appreciated that a wide range of other such groups are known in the art.

Finally the permanent side-chain protecting groups are removed and the peptide is cleaved from the resin, usually simultaneously through treatment with a suitable acidic reagent, e.g. trifluoroacetic acid (TFA).

Peptidic vectors containing multiple bridges are synthesised using different cysteine protecting groups so that no ambiguity exists as to the final folded form of the vector. The synthesis disclosed in WO03/006491, describing how the peptides, including thioether and disulphide bridges are formed, may be used. Thioether cyclisation may e.g. be carried out in the following way: The Cys(t-Bu)-protected peptide is dissolved in water/acetonitril (1 mg/ml). The mixture is adjusted to pH 8 using diluted ammonia solution and the mixture is stirred over night. Disulphide bridges may be formed by DMSO/THF oxidation in the following way: The peptide is dissolved in 5% DMSO/TFA (1 mg/ml) and the mixture is stirred for 30 minutes.

Conjugation of $W_1$ and/or $X_7$ to the peptide:

$W_1$ and/or $X_7$ can be conjugated to the peptide using all the known methods of chemical synthesis. Particularly useful is the nucleophile substitution reaction where a leaving group on the peptide N-terminus is replaced by a nucleophilic group on $W_1$ and/or $X_7$. Such a leaving group may be a bromide attached in alpha position to a carbonyl group, and such a nucleophile may be nitrogen.

Conjugation of Z to the peptide, to $W_1$ and/or $X_7$:

Z can be conjugated directly to the peptide using the same methods as for the conjugation of $W_1$ and/or $X_7$ to the peptide. In the case where Z is attached to the peptide via $W_1$ or $X_7$ any methods of chemical synthesis may be used, in the conjugation of Z and $W_1$ or $X_7$. Particularly useful is amide bond formation.

The peptide vector and peptide-based compounds may be purified using high performance liquid chromatography (HPLC) and characterised by mass spectrometry and analytical HPLC before testing in the in vitro screen.

The present invention will now be further illustrated by way of the following non-limiting examples.

EXAMPLES

Example 1

Conjugate of [$Cys^{2-8}$] cyclo[$CH_2CONH$-Asp-Cys-Arg-Gly-Asp-Cys]-Phe-Cys-Gly-NH-$(CH_2CH_2O)_2$ $CH_2CH_2NH_2$ and crba-Pn216 chelate 1 a) Synthesis of $ClCH_2CONH$-Asp-Cys(tBu)-Arg-Gly-Asp-Cys-Phe-Cys(tBu)-Gly-NH-$(CH_2CH_2O)_2$ $CH_2CH_2NH_2$

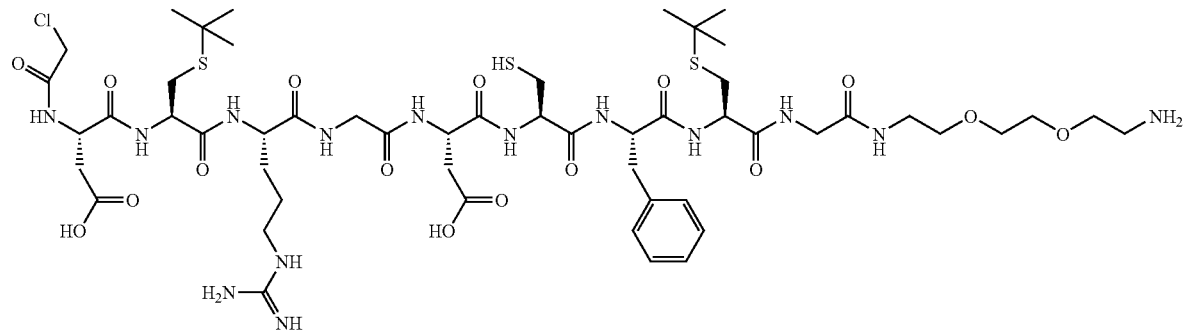

Molecular Weight = 1293.986
Exact Mass = 1292.512
Molecular Formula = C52H85ClN14O16S3

The peptide was synthesised on an ABI 433A automatic peptide synthesiser starting with O-Bis-(aminoethyl)ethylene glycol trityl resin on a 0.25 mmol scale using 1 mmol amino acid and chloroacetic acid cartridges. The amino acids and chloroacetic acid were pre-activated using HBTU before coupling. The simultaneous removal of peptide and side-chain protecting groups (except tBu) from the resin was carried out in TFA containing TIS (5%), $H_2O$ (5%) and phenol (2.5%) for two hours.

After work-up crude peptide was obtained as a white solid (Analytical HPLC: Gradient, 5-50% B over 10 min where A=$H_2O$/0.1% TFA and B=$CH_3CN$/0.1% TFA; column, Phenomenex Luna 3μ C18 50×4.6 mm; detection, UV 214 nm; product retention time, 6.50 min). Further product characterisation was carried out using electrospray mass spectrometry (expected, M+H at 1293.5, found, at 1293.5).

1 b) Synthesis of cyclo[$CH_2CONH$-Asp-Cys(tBu)-Arg-Gly-Asp-Cys]-Phe-Cys(tBu)-Gly-NH-($CH_2CH_2O)_2CH_2CH_2NH_2$

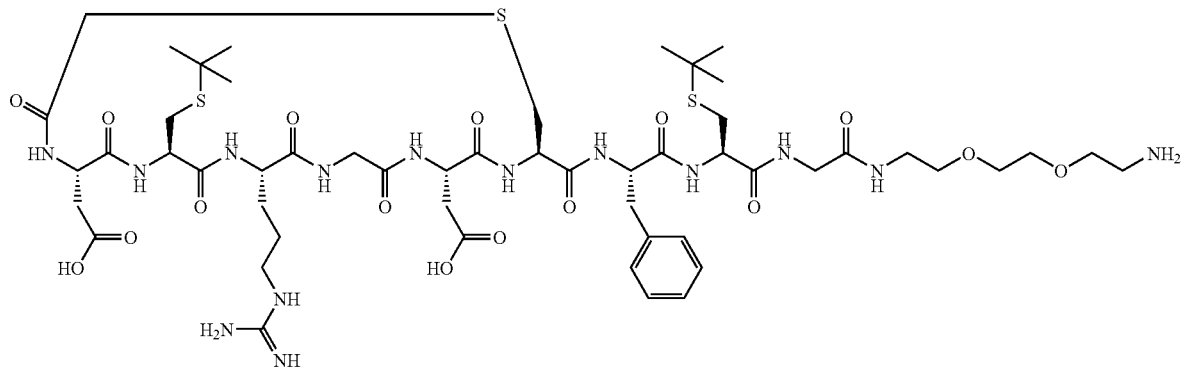

Molecular Weight = 1257.525
Exact Mass = 1256.535
Molecular Formula = C52H84N14O16S3

$ClCH_2CONH$-Asp-Cys(tBu)-Arg-Gly-Asp-Cys-Phe-Cys(tBu)-Gly-NH-($CH_2CH_2O)_2CH_2CH_2NH_2$ was dissolved in water/acetonitrile. The mixture was adjusted to pH 8 with ammonia solution and stirred for 4 hours. After work-up crude peptide was obtained as a white solid (Analytical HPLC: Gradient, 5-50% B over 10 min where A=$H_2O$/0.1% TFA and B=$CH_3CN$/0.1% TFA; column, Phenomenex Luna 3 μC18 50×4.6 mm; detection, UV 214 nm; product retention time, 5.90 min). Further product characterisation was carried out using electrospray mass spectrometry (expected, M+H at 1257.5, found, at 1257.5).

1 c) Synthesis of [$Cys^{2-8}$] cyclo[$CH_2CONH$-Asp-Cys-Arg-Gly-Asp-Cys]-Phe-Cys-Gly-NH-($CH_2CH_2O)_2CH_2CH_2NH_2$

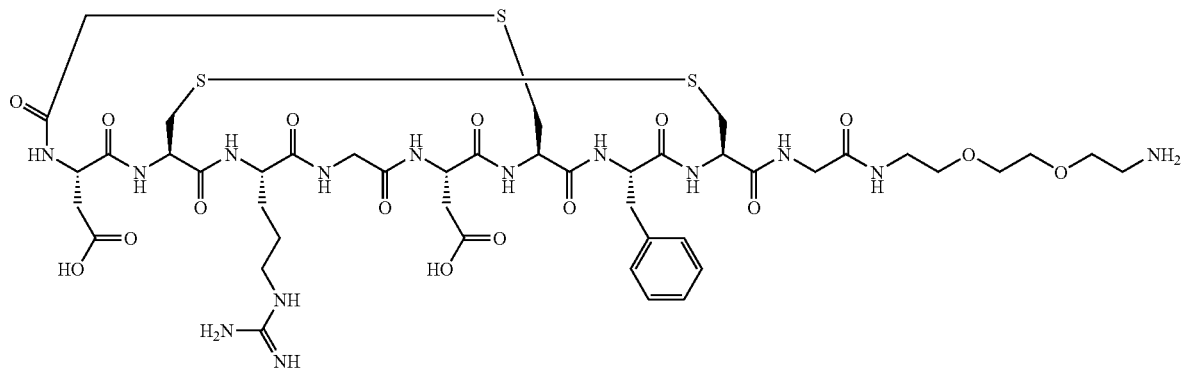

Molecular Weight = 1143.293
Exact Mass = 1142.394
Molecular Formula = C44H66N14O16S3

Cyclo[CH$_2$CONH-Asp-Cys(tBu)-Arg-Gly-Asp-Cys(tBu)-Phe-Cys]-Gly-NH-(CH$_2$CH$_2$O)$_2$CH$_2$CH$_2$NH$_2$ was dissolved in TFA (200 ml) containing anisole (500 µl), DMSO (4 ml). The mixture was stirred for 15 min following which the TFA was removed in vacuo and the peptide precipitated by the addition of diethyl ether. Purification by preparative HPLC (Phenomenex Luna 5µ C18 (2) 250×21.20 mm column) of the crude material was carried out using 0-30% B, where A=H$_2$O/0.1% TFA and B=CH$_3$CN/0.1% TFA, over 40 min at a flow rate of 10 mL/min. After lyophilisation 18.7 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 50×4.6 mm; detection, UV 214 nm; product retention time, 5.73 min). Further product characterisation was carried out using electrospray mass spectrometry (expected, M+H at 1143.4, found, at 1143.5).

1 d) Conjugation of Peptide and Carba-Pn216 Chelate

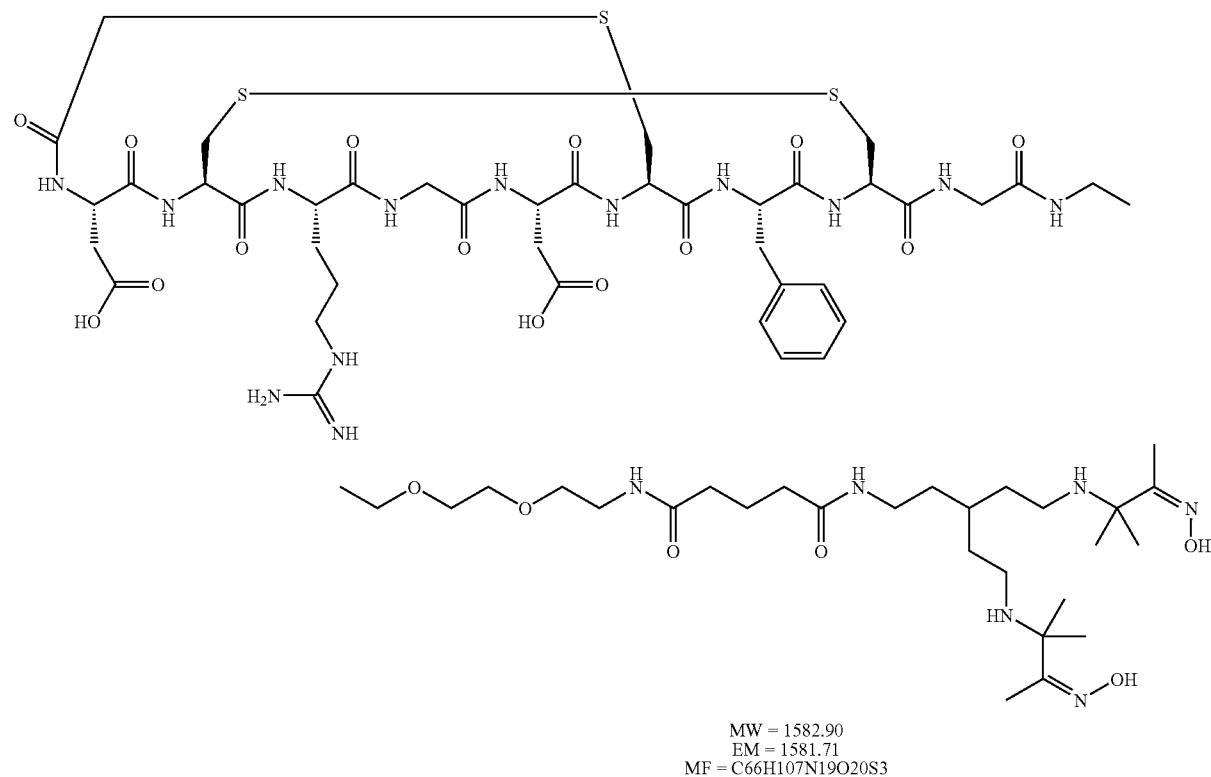

MW = 1582.90
EM = 1581.71
MF = C66H107N19O20S3

Carba-Pn216 chelate active ester, N-methylmorpholine and [Cys$^{2-8}$] cyclo[CH$_2$CONH-Asp-Cys-Arg-Gly-Asp-Cys]-Phe-Cys-Gly-NH(CH$_2$CH$_2$O)$_2$CH$_2$CH$_2$NH$_2$ are dissolved in N,N-dimethylformamide (0.5 ml). The mixture is stirred for 24 hours. Water is added and the product purified by preparative HPLC.

Example 2

Conjugate of [Cys$^{2-8}$] cyclo[CH$_2$CONH-Lys-Cys-Arg-Gly-Arg-Cys]-Phe-Cys-CCX$_6$-NH$_2$ and carba-Pn216 chelate 2 a) Synthesis of ClCH$_2$CONH-Lys-Cys(tBu)-Arg-Gly-Asp-Cys-Phe-Cys(tBu)-CCX$_6$-NH$_2$

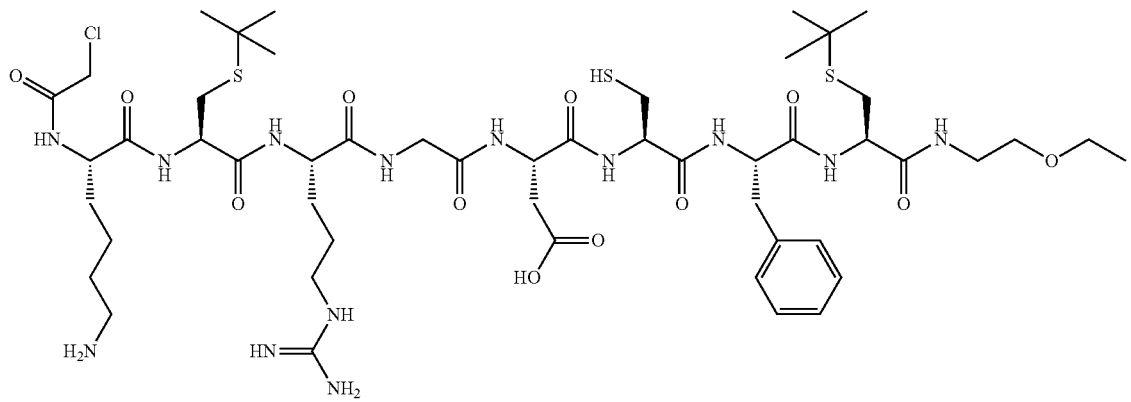

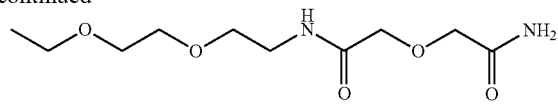

The peptide is synthesised on an ABI 433A automatic peptide synthesiser starting with Rink Amide AM resin on a 0.25 mmol scale using 1 mmol amino acid and chloroacetic acid cartridges. The amino acids and chloroacetic acid are pre-activated using HBTU before coupling. The simultaneous removal of peptide and side-chain protecting groups (except tBu) from the resin is carried out in TFA containing TIS (5%), H$_2$O (5%) and phenol (2.5%) for two hours. After work-up, crude peptide is obtained as a white solid.

2 b) Synthesis of Cyclo[CH$_2$CONH-Lys-Cys(tBu)-Arg-Gly-Asp-Cys]-Phe-Cys(tBu)-CCX$_6$-NH$_2$

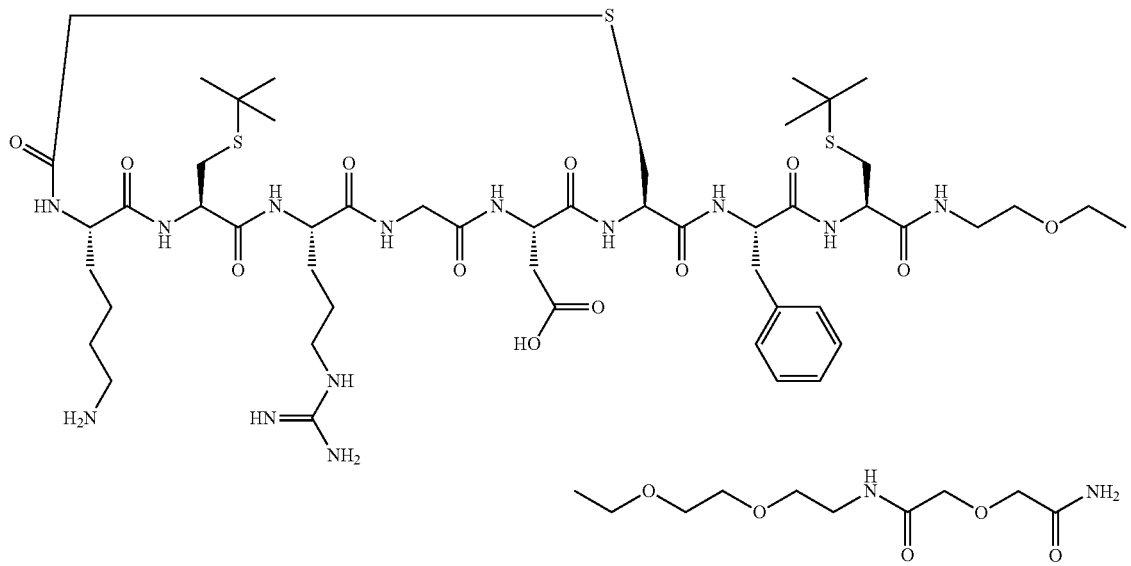

ClCH$_2$CONH-Lys-Cys(tBu)-Arg-Gly-Asp-Cys-Phe-Cys(tBu)-CCX$_6$-NH$_2$ is dissolved in water/acetonitrile. The mixture is adjusted to pH 8 with ammonia solution and stirred for 4 hours. Crude peptide is obtained as a white solid after lyophilisation.

2 c) Synthesis of [Cys$^{2-8}$] cyclo[CH$_2$CONH-Lys-Cys-Arg-Gly-Asp-Cys]-Phe-Cys-CCX$_6$-NH$_2$

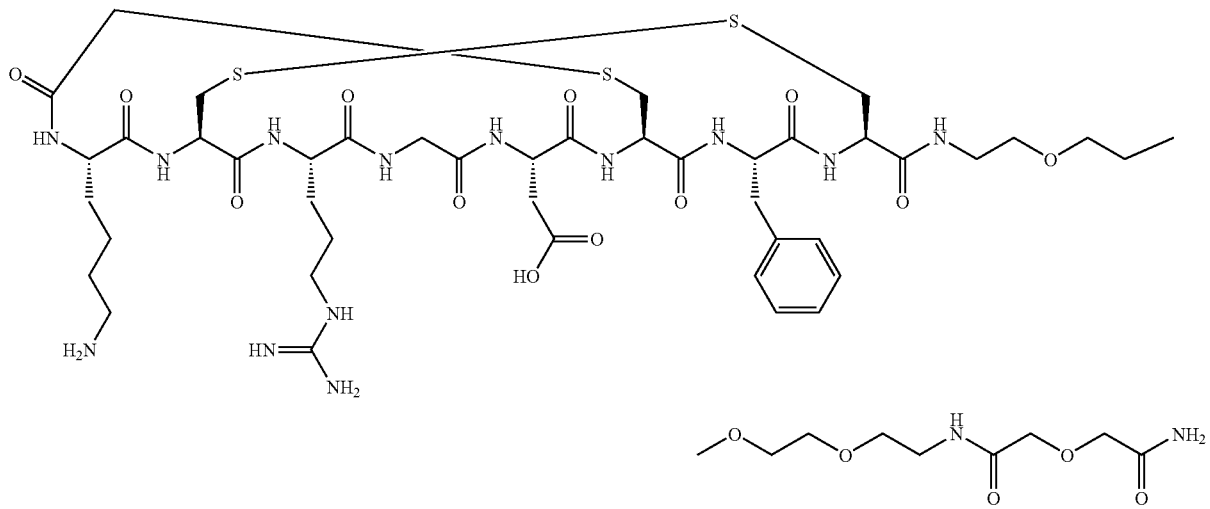

Cyclo[CH$_2$CONH-Lys-Cys(tBu)-Arg-Gly-Asp-Cys]-Phe-Cys(tBu)-CCX$_6$-NH$_2$ is dissolved in TFA (200 ml) containing DMSO (4 ml). The mixture is stirred for 30 min following which the TFA is removed in vacuo and the peptide precipitated by the addition of diethyl ether.

2 d) Conjugation of Peptide and Carba-Pn216 Chelate

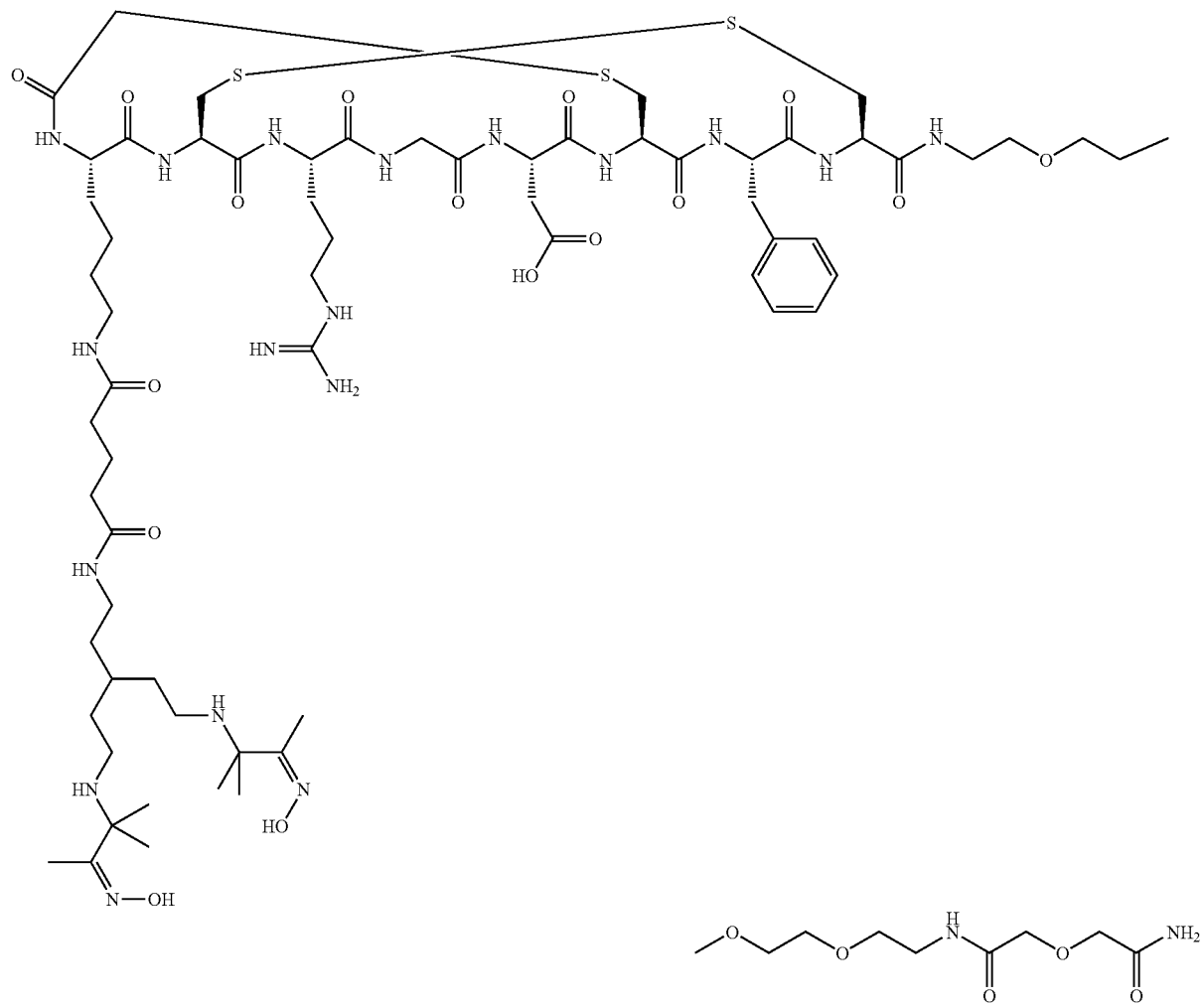

Carba-Pn216 chelate active ester, N-methylmorpholine and [Cys$^{2-8}$] cyclo[CH$_2$CONH-Lys-Cys-Arg-Gly-Asp-Cys]-Phe-Cys-CCX$_6$-NH$_2$ are dissolved in N,N-dimethylformamide (0.5 ml). The mixture is stirred for 24 hours. Water is added and the product purified by preparative HPLC.

---

The invention claimed is:

1. A compound of general formula (I)

$$R_a-C(=O)-\overset{\overset{Z_1-W_1}{|}}{\underset{\underset{S\text{————————————}(CH_2)_h}{|}}{X_1}}-\overset{\overset{S\text{————————}S}{|}}{X_2}-X_3-G-D-X_4-X_5-X_6-X_7-Z_2 \quad (I)$$

and pharmaceutically acceptable salt thereof
wherein

G represents glycine

D represents aspartic acid $R_a$ represents $-(CH_2)_n-$ or $-(CH_2)_n-C_6H_4-$ wherein n represents a positive integer 1 to 10 h represents a positive integer 1 or 2

$X_1$ represents an amino acid residue wherein said amino acid possesses a functional side-chain, $X_2$ and $X_6$ represent independently amino acid residues together forming a disulphide bond, $X_3$ represents, N-methylarginine, $X_4$ represents a thiol-containing amino acid residue, and $X_5$ represents a hydrophobic amino acid, and $X_7$ is absent or a biomodifier moiety, wherein said biomodifier comprises 1-10 units of a monodisperse PEG building block, 1 to 10 amino acid residues or 1-10 units of formula (II)

$$\left[H_2N\diagdown\diagup O\diagdown\diagup O\diagdown\diagup O\diagdown\diagup\underset{H}{N}\diagdown\underset{O}{\overset{}{C}}\diagdown O\diagdown\underset{O}{\overset{}{C}}\right]_m \quad (II)$$

where m equals an integer from 1 to 10, $Z_1$ and $Z_2$ are each independently a Z group or is absent, Z is a PET or SPECT radionuclide imaging moiety, with the proviso that at least one $Z_1$ or $Z_2$ group is present, and $W_1$ represents a spacer moiety when Z1 is present.

2. A compound as claimed in claim 1 wherein any of the amino acid residues are independently in the D or L conformation.

3. A compound as claimed in claim 1 wherein $R_a$ represents $-(CH_2)-$.

4. A compound as claimed in claim 1 wherein $X_1$ represents aspartic acid, glutamic acid, lysine, or homolysine.

5. A compound as claimed in claim 1 wherein $X_2$, $X_4$ and $X_6$ independently represent a cysteine or homocysteine residue.

6. A compound as claimed in claim 1 wherein $X_3$ represents arginine.

7. A compound as claimed in claim 1 wherein $X_5$ represents a tyrosine, phenylalanine, 3-iodo-tyrosine or naphthylalanine.

8. A compound as claimed in claim 1 where $W_1$ is glutaric or succinic acid.

9. A pharmaceutical composition comprising an effective amount of a compound of claim 1, together with one or more pharmaceutically acceptable adjuvants, excipients or diluents.

10. A method of generating images of a human or animal body, said method comprising (a) administering a contrast agent comprising the compound of claim 1 and (b) generating an image of at least a part of said body to which said contrast agent has distributed.

11. A method of monitoring the effect of treatment of a human or animal body, said method comprising (a) administering to said body a contrast agent comprising the compound of claim 1; (b) detecting the uptake of said contrast agent by cell receptors; and (c) optionally, repeating said administering and said detecting steps.

* * * * *

SEQUENCE LISTING

<160> NUMBER OF SEQ ID NOS: 5

<210> SEQ ID NO 1
<211> LENGTH: 8
<212> TYPE: PRT
<213> ORGANISM: Artificial sequence

```
<220> FEATURE:
<223> OTHER INFORMATION: Synthesised peptide
<220> FEATURE:
<221> NAME/KEY: MISC_FEATURE
<222> LOCATION: (1)..(1)
<223> OTHER INFORMATION: Amino acid with functional side-chain
<220> FEATURE:
<221> NAME/KEY: MISC_FEATURE
<222> LOCATION: (2)..(2)
<223> OTHER INFORMATION: Amino acid residue capable of forming a
      disulphide bond
<220> FEATURE:
<221> NAME/KEY: MISC_FEATURE
<222> LOCATION: (3)..(3)
<223> OTHER INFORMATION: Arginine, N-methylarginine or arginine mimetic
<220> FEATURE:
<221> NAME/KEY: MISC_FEATURE
<222> LOCATION: (6)..(6)
<223> OTHER INFORMATION: A thiol-containing amino acid
<220> FEATURE:
<221> NAME/KEY: MISC_FEATURE
<222> LOCATION: (7)..(7)
<223> OTHER INFORMATION: A hydrophobic amino acid
<220> FEATURE:
<221> NAME/KEY: MISC_FEATURE
<222> LOCATION: (8)..(8)
<223> OTHER INFORMATION: Amino acid residue capable of forming a
      disulphide bond

<400> SEQUENCE: 1

Xaa Xaa Xaa Gly Asp Xaa Xaa Xaa
1               5

<210> SEQ ID NO 2
<211> LENGTH: 9
<212> TYPE: PRT
<213> ORGANISM: Artificial sequence
<220> FEATURE:
<223> OTHER INFORMATION: Synthesised peptide

<400> SEQUENCE: 2

Asp Cys Arg Gly Asp Cys Phe Cys Gly
1               5

<210> SEQ ID NO 3
<211> LENGTH: 9
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (1)..(1)
<223> OTHER INFORMATION: CH2CONH-Aspartic acid
<220> FEATURE:
<221> NAME/KEY: THIOETH
<222> LOCATION: (1)..(6)
<223> OTHER INFORMATION: Thioether bridge between residue 1 and 6
<220> FEATURE:
<221> NAME/KEY: DISULFID
<222> LOCATION: (2)..(8)
<223> OTHER INFORMATION: Disulphide bridge between residues 2 and 8

<400> SEQUENCE: 3

Xaa Cys Arg Gly Asp Cys Phe Cys Gly
1               5

<210> SEQ ID NO 4
<211> LENGTH: 9
<212> TYPE: PRT
<213> ORGANISM: Artificial sequence
<220> FEATURE:
<223> OTHER INFORMATION: Synthesised peptide
```

```
<220> FEATURE:
<221> NAME/KEY: MISC_FEATURE
<222> LOCATION: (1)..(1)
<223> OTHER INFORMATION: CH2CONH-Lysine
<220> FEATURE:
<221> NAME/KEY: THIOETH
<222> LOCATION: (1)..(6)
<223> OTHER INFORMATION: Thioether cyclisation between position 1 and 6
<220> FEATURE:
<221> NAME/KEY: DISULFID
<222> LOCATION: (2)..(8)
<223> OTHER INFORMATION: Disulphide bridge between residues 2 and 8

<400> SEQUENCE: 4

Xaa Lys Cys Arg Gly Asp Cys Phe Cys
1               5

<210> SEQ ID NO 5
<211> LENGTH: 9
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (1)..(1)
<223> OTHER INFORMATION: CH2CONH-Lysine

<400> SEQUENCE: 5

Xaa Lys Cys Arg Gly Asp Cys Phe Cys
1               5
```